(12) United States Patent
Boira Bonhora et al.

(10) Patent No.: US 11,596,702 B2
(45) Date of Patent: Mar. 7, 2023

(54) CONTAINER FOR STERILIZING FLEXIBLE BAGS

(71) Applicant: Grifols Worldwide Operations Limited, Dublin (IE)

(72) Inventors: Jordi Boira Bonhora, Parets del Valles (ES); Carlos Roura Salietti, Parets del Valles (ES)

(73) Assignee: Grifols Worldwide Operations Limited, Dublin (IE)

( * ) Notice: Subject to any disclaimer, the term of this patent is extended or adjusted under 35 U.S.C. 154(b) by 298 days.

(21) Appl. No.: 16/833,404

(22) Filed: Mar. 27, 2020

(65) Prior Publication Data
US 2020/0324008 A1   Oct. 15, 2020

(30) Foreign Application Priority Data
Apr. 15, 2019   (EP) .................................... 19382291

(51) Int. Cl.
*A61L 2/26*    (2006.01)
*A61L 2/00*    (2006.01)

(52) U.S. Cl.
CPC ................. *A61L 2/26* (2013.01); *A61L 2/007* (2013.01); *A61L 2/0035* (2013.01); *A61L 2202/121* (2013.01); *A61L 2202/122* (2013.01); *A61L 2202/21* (2013.01); *A61L 2202/23* (2013.01)

(58) Field of Classification Search
None
See application file for complete search history.

(56) References Cited

U.S. PATENT DOCUMENTS

| | | | |
|---|---|---|---|
| 3,596,430 A | | 8/1971 | Parish |
| 3,780,738 A | * | 12/1973 | Deaton ............... A61M 1/0001 |
| | | | 604/319 |
| 3,872,868 A | * | 3/1975 | Kline .................... A61J 1/1462 |
| | | | 248/688 |
| 4,415,085 A | * | 11/1983 | Clarke .................. B29C 66/133 |
| | | | 211/84 |
| 4,470,264 A | | 9/1984 | Morris |

(Continued)

FOREIGN PATENT DOCUMENTS

| | | |
|---|---|---|
| CL | 201703501 | 4/2018 |
| CN | 2917640 Y | 7/2007 |

(Continued)

OTHER PUBLICATIONS

Partial European Search Report in corresponding European Patent Application No. 19382291 dated Oct. 18, 2019.

*Primary Examiner* — Donald R Spamer
(74) *Attorney, Agent, or Firm* — Knobbe, Martens, Olson & Bear LLP

(57) ABSTRACT

A container for sterilizing flexible bags can be for pharmaceutical use. The container includes an upper flat structure including at least one element supporting the flexible bags and designed to accommodate a plug port of the flexible bag. The support element includes at least one fastening element, which is suitable for retaining the flexible bags once they are inserted into the support element. The container also includes a lower receptacle designed to contain the upper flat structure and to couple to the upper flat structure in a detachable manner. The container further includes a cap for hermetically sealing the lower receptacle.

15 Claims, 9 Drawing Sheets

(56) References Cited

U.S. PATENT DOCUMENTS

| | | | |
|---|---|---|---|
| 4,565,073 A | | 1/1986 | Lavender |
| 5,882,602 A | * | 3/1999 | Savage ................ B01L 3/0293 |
| | | | 422/537 |
| 5,922,278 A | * | 7/1999 | Chapman ............ A61M 1/3681 |
| | | | 250/455.11 |
| 6,419,088 B1 | | 7/2002 | Barrois |
| 10,588,990 B2 | | 3/2020 | Tamarindo |
| 10,661,929 B2 | * | 5/2020 | Gebbink ............ B65D 75/5883 |
| 2003/0136697 A1 | * | 7/2003 | Nix ........................... A61J 1/16 |
| | | | 206/459.5 |
| 2010/0307956 A1 | | 12/2010 | Lepot |
| 2015/0095047 A1 | * | 4/2015 | Burrows ............... A61J 7/0436 |
| | | | 206/534 |
| 2015/0113919 A1 | | 4/2015 | Provitera |
| 2016/0153691 A1 | * | 6/2016 | Mean ...................... F25D 25/00 |
| | | | 62/457.9 |
| 2018/0126066 A1 | * | 5/2018 | Narvekar ................ B65B 55/04 |
| 2018/0134423 A1 | | 5/2018 | Narvekar et al. |
| 2021/0015706 A1 | * | 1/2021 | Wabel ................ A61M 1/1668 |

FOREIGN PATENT DOCUMENTS

| | | |
|---|---|---|
| DE | 10 2004 032306 A1 | 2/2006 |
| DE | 102015012861 A1 | 4/2017 |
| EP | 0171550 A1 | 2/1986 |
| EP | 0732097 A2 | 9/1996 |
| EP | 2266522 A1 | 12/2010 |
| EP | 3269409 B1 | 2/2019 |
| ES | 2248768 T3 | 3/2006 |
| FR | 2482566 A1 | 11/1981 |
| FR | 2759985 A1 | 8/1998 |
| JP | 2018-089171 A | 6/2018 |
| WO | WO 2000/005146 A1 | 2/2000 |
| WO | 2017139385 A1 | 8/2017 |

\* cited by examiner

CONTAINER FOR STERILIZING FLEXIBLE BAGS

BACKGROUND

The present invention relates to the pharmaceutical industry, in particular to a new container for sterilizing flexible bags for pharmaceutical use. More specifically, the present invention discloses a "nest" type container for sterilizing flexible bags containing products derived from human plasma for therapeutic use.

SUMMARY

Recently in the pharmaceutical industry in general and, in particular, in the industry of products obtained from human plasma, proof exists that plastic containers, in particular flexible plastic bags, are also useful as final packaging for hemoderivatives for several reasons: they are easy to shape, giving them great versatility and adaptability in their design, are rupture-resistant, ergonomic, and, due to their low density and weight, provide important costs savings regarding transportation and logistics. Furthermore, they are flexible and easy to handle. Therefore, they are in demand in the public health sector.

Another advantage of flexible plastic bags is that they are compatible with sterilization by radiation, either by means of gamma rays or electron beam (E-beam). Currently there are solutions for hemoderivatives commercialized in plastic bags (e.g. Flexbumin®, a 20% solution of human plasma albumin, traded by Baxalta Spain S.L.) available on the market.

Usually, said flexible plastic bags are sterilized prior to the filling thereof by means of irradiation with gamma rays or electron beam (E-beam). Sterilization by radiation as ionising radiation is commonly used in hospitals for sanitary devices (e.g. catheters, surgical items, and critical care tools). Gamma irradiation is the most popular form of sterilization by radiation and is typically used when the materials are sensitive to the high temperature of the autoclave.

In addition, it is increasingly common for rigid containers, also known as "nest" containers, to be used for sterilizing surgical material, syringes, or vials. These containers are cost-effective, reusable, easy to transport and to clean, and are very effective in the sterilization process. However, these known containers are not suitable for sterilizing bags, due to the lack of rigidity and the fragility thereof.

For instance, the document of European Patent EP 3269409B1 discloses a container for sterilizing syringes and the PCT application WO 2017/139385 A1 discloses a device for facilitating the correct position of syringes and a product inspection path. Although the two documents disclose containers for sterilizing syringes, it is not possible to incorporate flexible bags in said containers for the sterilization of said bags.

In addition, the document of Spanish Patent ES 2248768T3 discloses a packaging intended to be used to transport sterile objects or objects to be sterilized, comprising a box intended to receive the sterile objects or objects to be sterilized and a cover sheet of selectively airtight material, which sheet is fixed above the box such that it will seal the latter in an airtight manner. This packaging is not suitable for flexible bags either.

Therefore, there exists the need provide "nest" type containers for sterilizing and transporting flexible plastic bags for pharmaceutical use, in particular flexible plastic bags that will contain human plasma by-products. The use of this type of containers for sterilizing and transporting flexible plastic bags is not known to the inventors of the present invention.

Surprisingly, the inventors of the present invention have developed a "nest" type container suitable for sterilizing and transporting flexible plastic bags, which, in addition to the above advantages of these types of containers, allows said bags to be fastened by the plug region of said bags and is suitable for being filled both manually and automatically.

Therefore, in a first aspect, the present invention discloses a "nest" type container for sterilizing flexible bags for pharmaceutical use, comprising:
  a) an upper flat structure comprising at least one support element of said flexible bags which is designed to accommodate the port-plug structure of said flexible bag, said support element comprising at least one fastening element which is suitable for retaining said bags once they are inserted into said support element;
  b) a lower receptacle which is designed to contain the upper flat structure (a) and to couple thereto in a detachable manner;
  c) a cap for hermetically sealing said lower receptacle.

Preferably, said upper structure is also the cap for hermetically sealing the lower receptacle.

Preferably, the container of the present invention can accommodate between 1 and 250 flexible bags, more preferably between 1 and 180 flexible bags.

It is obvious to the skilled person that the shape of the container of the present invention can be any one suitable for sterilization. Preferably, said container has the shape of a rectangular parallelepipedon.

It is also clear that the material for producing said container can be any material suitable for sterilization, such as plastics material. Preferably, said container is made from high-density polyethylene (HDPE).

Preferably, said support element of the flexible bags are bars with a T and/or L-shaped cross-section which are attached to the upper flat structure of the container of the present invention in an undetachable manner.

It is also preferable for said fastening element to be a semi-circle-shaped notch in said support elements. Said semi-circle must have a diameter greater than the port of the flexible bag but must be smaller than the diameter of the flange of the cap of said bag.

BRIEF DESCRIPTION OF THE DRAWING

The invention will be explained below with reference to the figures, by way of explanatory, non-restrictive example, of various embodiments of the device of the present invention, in which.

DETAILED DESCRIPTION

Figure 1:
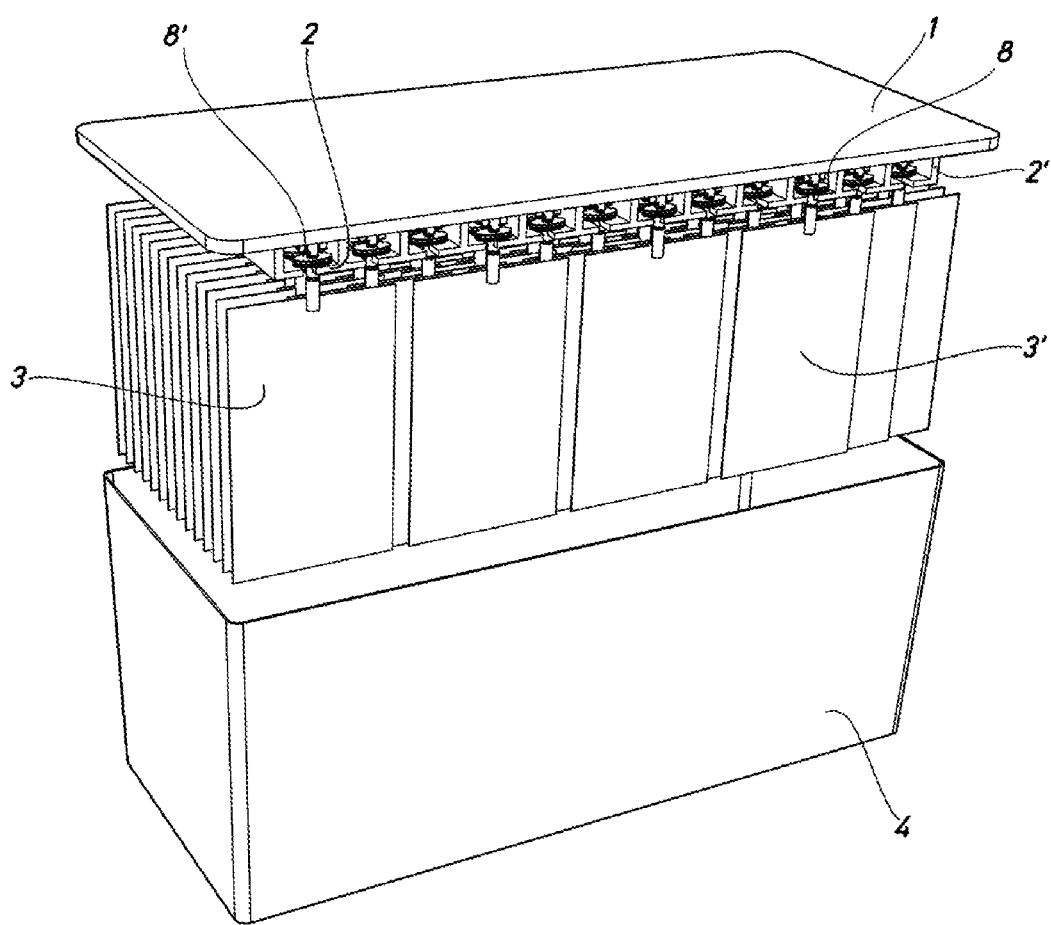
FIG. 1 is a perspective view of an embodiment of the container for sterilizing flexible bags of the present invention.

As seen in FIG. 1, the container for sterilizing flexible bags of the present invention is formed by an upper flat structure -1-, in which the lower part has the support elements -2-, -2'- of said flexible bags -3-, -3'-, which elements are designed to accommodate the port-plug structure -8-, -8'- of said flexible bags -3-, -3'-, and a lower receptacle -4- in the shape of a rectangular parallelepipedon which is designed to accommodate the upper flat structure -1-, which in this case also acts as a cap for hermetically sealing said lower receptacle -4-.

Figure 2:
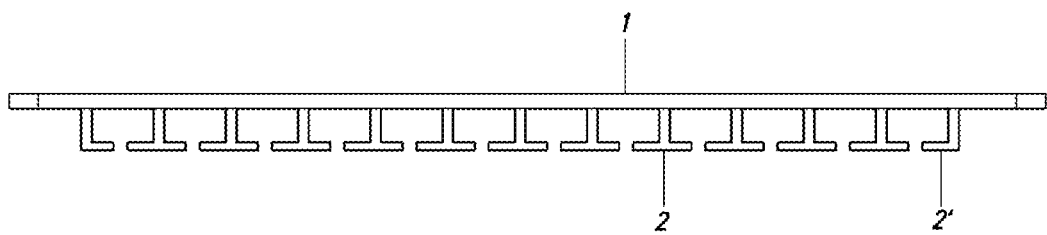
FIG. 2 is a front view of a first embodiment of the upper flat structure of the container for sterilizing flexible bags of the present invention.

FIG. 2 shows a first embodiment of the upper flat structure -1-, in which the lower part thereof has support elements -2-, -2'- of said flexible bags.

Figure 3:
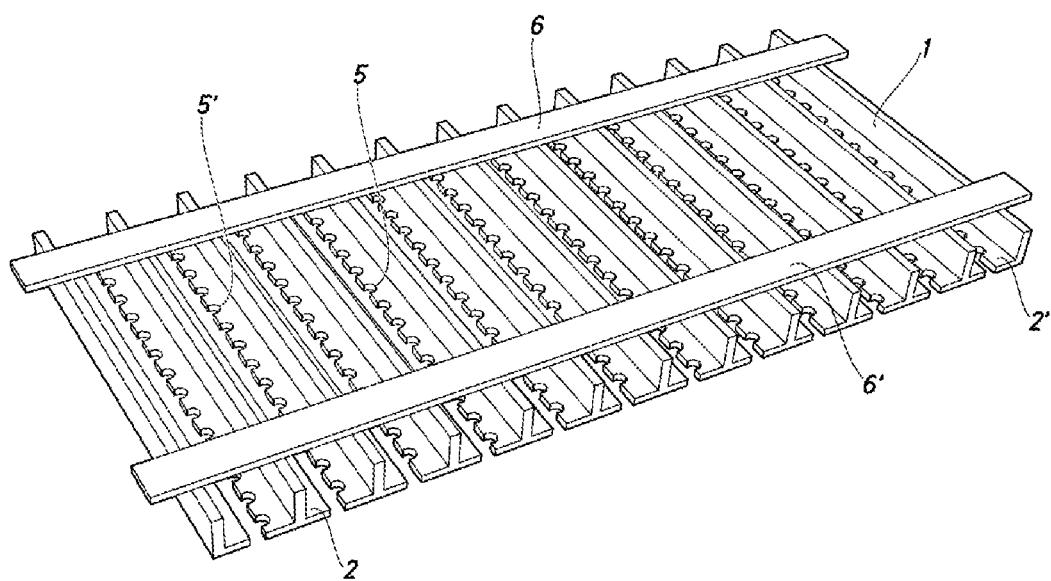
FIG. 3 is a perspective view of a second embodiment of the upper flat structure of the container for sterilizing flexible bags of the present invention.

FIG. 3 is a perspective view of a second embodiment of the upper flat structure -1- of the container for sterilizing flexible bags of the present invention. It also shows that the support elements -2-, -2'- are attached to each other by two bars -6-, -6'- parallel to each other and perpendicular to said support elements -2-, -2'-. It also shows the fastening elements -5-, -5'- of the flexible bags in the shape of semi-circles arranged in the support elements -2-, -2'-.

Figure 4:
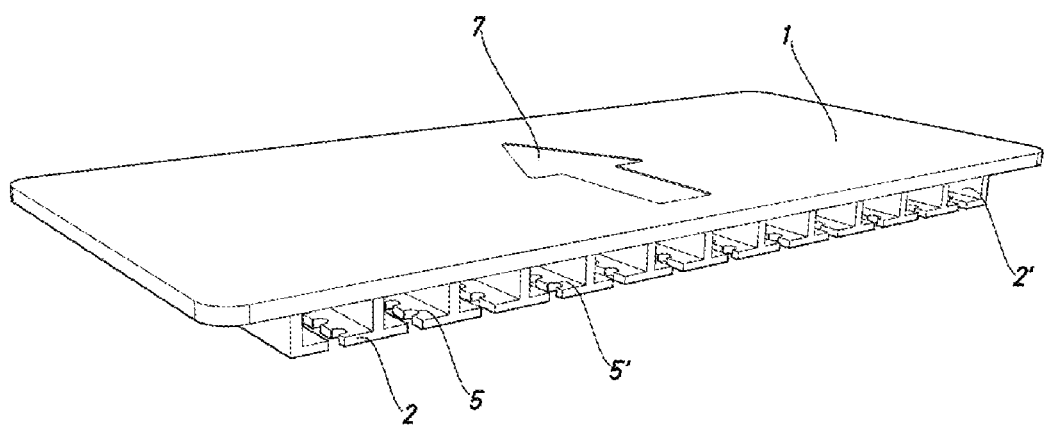
FIG. 4 is a perspective view of the first embodiment of the upper flat structure of the container for sterilizing flexible bags of the present invention.

In addition, FIG. 4 is a perspective view of the first embodiment of the upper flat structure of the container for sterilizing flexible bags of the present invention. In said figure, the upper flat structure -1- is also the cap for the hermetically sealing the lower receptacle of the container of the present invention. The support elements -2-, -2'-, which comprise the fastening elements -5-, -5'-, have the flexible bags in the lower part of said upper flat structure -1-. The arrow -7- indicates the direction in which the flexible bags will be placed in the upper flat structure -1- of the container of the present invention.

Figure 5:
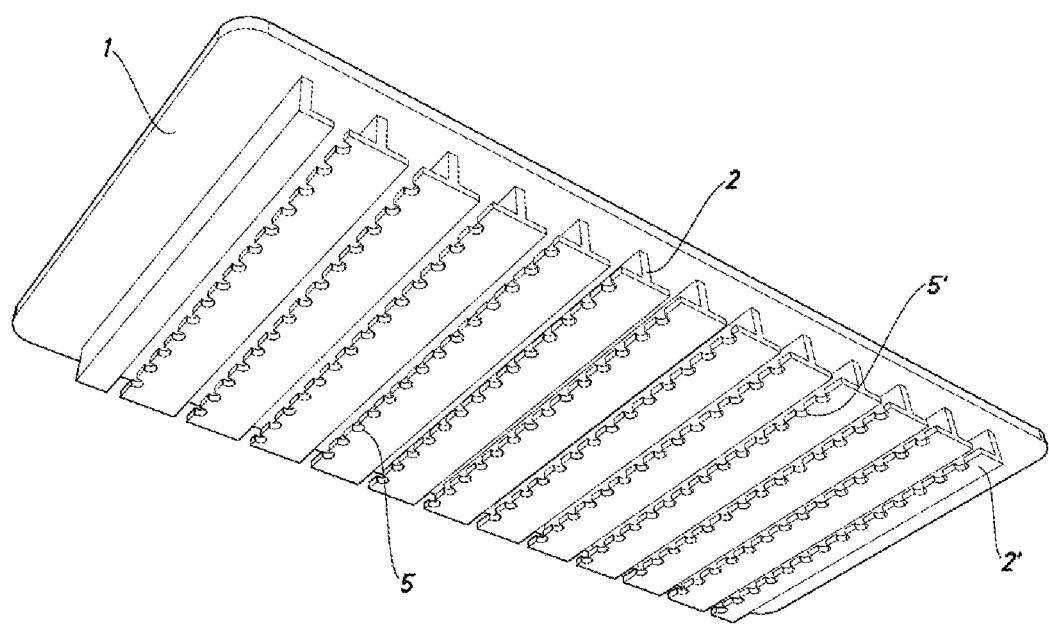
FIG. 5 is a perspective view of the lower part of the first embodiment of the upper flat structure of the container for sterilizing flexible bags of the present invention, shown in FIG. 4.

FIG. 5 is a perspective view of the lower part of the first embodiment of the upper flat structure of FIG. 4. It is noted how some of the support elements -2 can have the T-shaped cross-section and others -2'- have the L-shaped cross-section.

Figure 6:
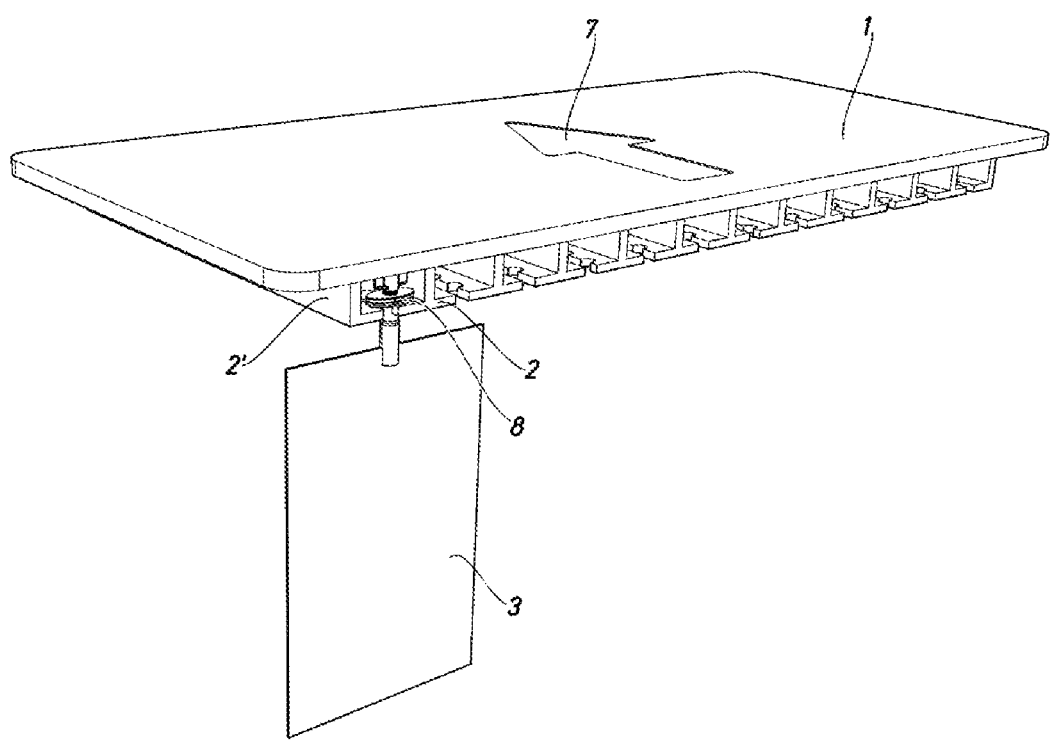
FIG. 6 is a perspective view of the first embodiment of the upper flat structure of the container for sterilizing flexible bags of the present invention, a bag having been placed.

FIG. 6 is a perspective view of the first embodiment of the upper flat structure -1- of the container for sterilizing flexible bags of the present invention, a flexible bag -3- having been placed. The port-plug structure -8- of said flexible bag -3- is inserted into the slot formed by the support elements -2-, -2'- and is moved in the direction of the arrow -7- as far as the furthermost fastening element (not shown in the figure) of the support elements -2-, -2'- through which said flexible bag -3- was inserted.

Figure 7:
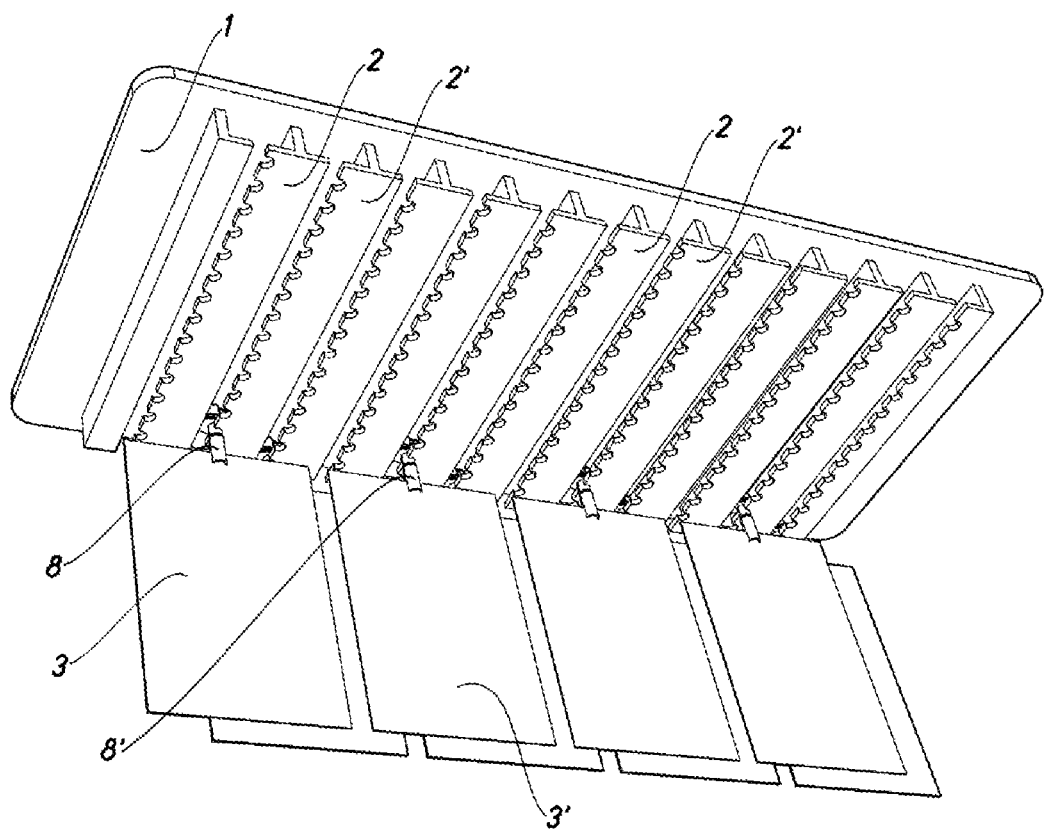
FIG. 7 is a perspective view of the lower part of the first embodiment of the upper flat structure of the container for sterilizing flexible bags of the present invention, the bags being alternately placed.

FIG. 7 is a perspective view of the first embodiment of the lower part of the upper flat structure -1- of the container for sterilizing flexible bags of the present invention, said flexible bags -3-, -3'- being alternately placed and the container being partially full. The port-plug structures -8-, -8'- of said flexible bags -3-, -3'-, after being inserted into the slots formed by the support elements -2-, -2'-, are accommodated in the fastening elements of the upper flat structure -1-.

Figure 8:
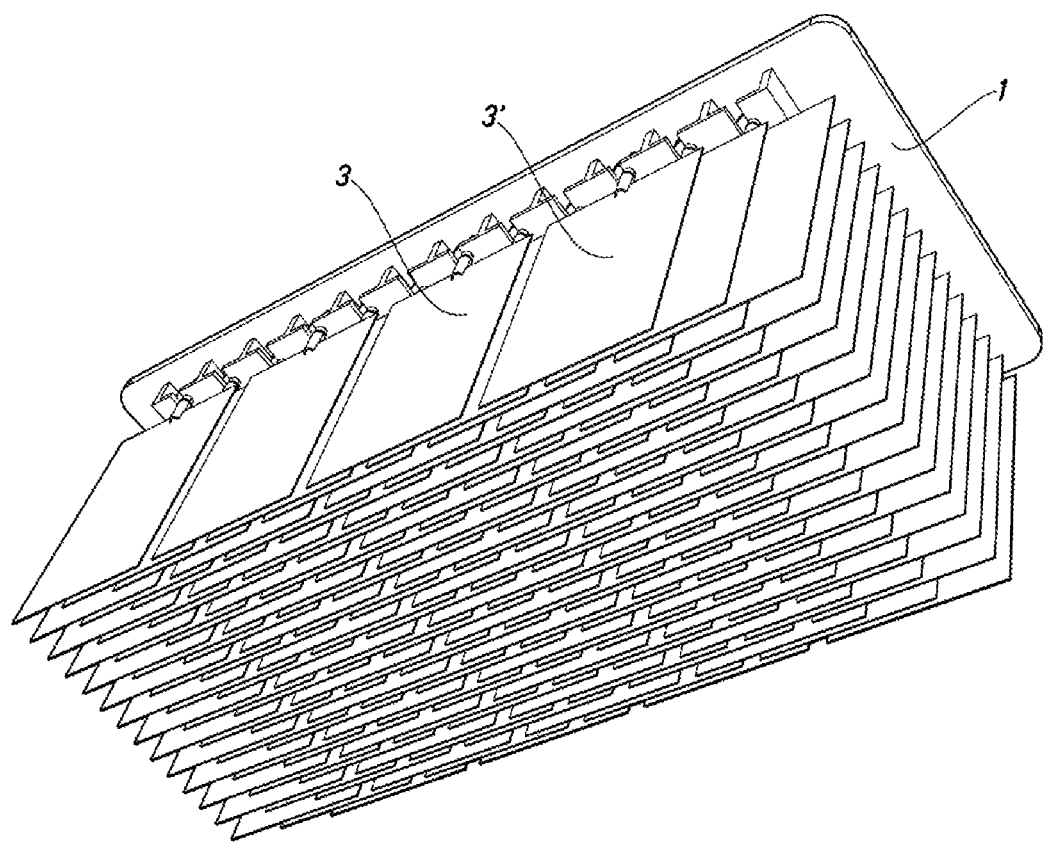
FIG. 8 is a perspective view of the lower part of the first embodiment of the upper flat structure of the container for sterilizing flexible bags of the present invention, all the bags to be sterilized having been placed.
Figure 9:
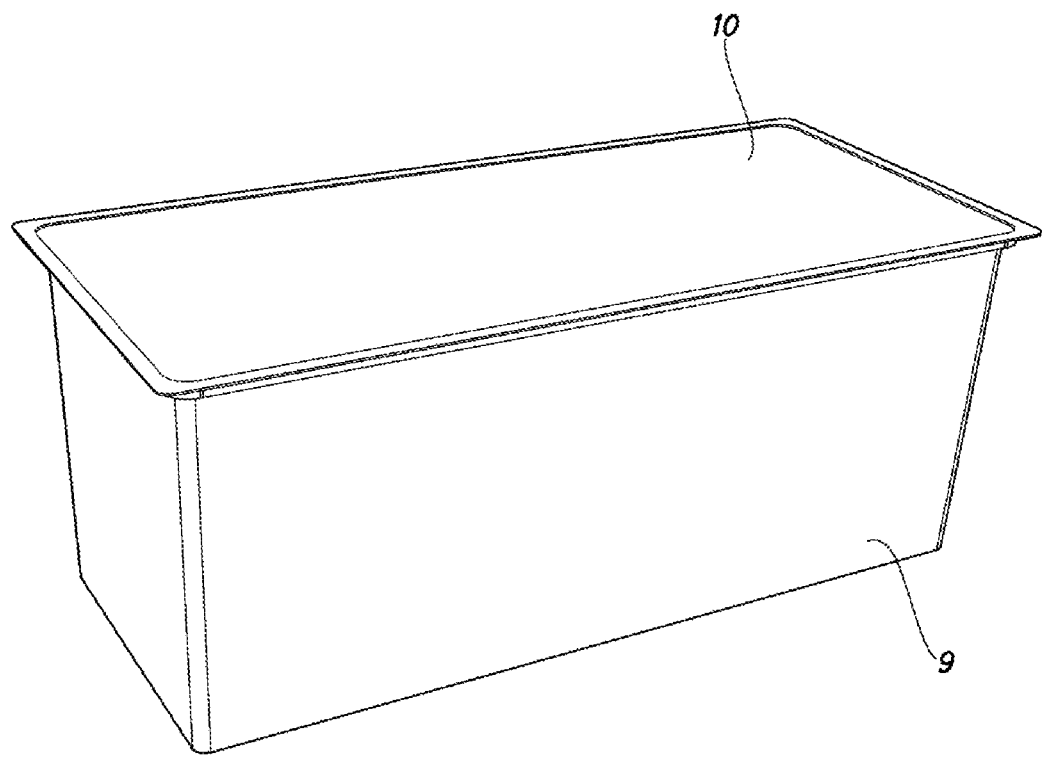
FIG. 9 is a perspective view of an embodiment of the container of the present invention when hermetically sealed.

FIG. 8 is a perspective view of the first embodiment of the lower part of the upper flat structure -1- of the container for sterilizing flexible bags of the present invention, all the flexible bags -3-, -3'- to be sterilized being placed in the upper flat structure -1-. Said upper flat structure is inserted into the lower receptacle -9- in order to obtain a container -10- for sterilizing said bags (as shown in FIG. 9), which is hermetically sealed for sterilizing and transporting the flexible bags arranged therein.

Finally, the present invention discloses a method for filling the container for the above-described sterilization of flexible bags, characterized in that it comprises the following steps:

a) inserting the port-plug structure of a flexible bag through the slot formed by the support elements of said flexible bags, which elements are located in the upper flat structure of said container;

b) placing said bag in the fastening element which is furthest from the insertion region of said bag through the support elements;

c) inserting new bags through the support elements until all fastening elements of the upper flat structure of said container are full;

d) inserting said upper flat structure into the lower receptacle of the container;

e) hermetically sealing said container and sterilizing the same.

Preferably, the new flexible bags are placed in such a way that the first row of bags in the fastening elements located in the support elements which are furthest from the insertion region of said bag is filled.

Preferably, the rows are alternately formed in order to place the highest number of bags possible inside the container of the present invention.

The sterilization in step (e) may be carried out through any suitable method by an expert in the field. Preferably, said sterilization is carried out by using gamma rays or electron beam (E-beam).

It is also preferable for the upper flat structure to be, at the same time, the cap of the lower receptacle of the container of the present invention and to be suitable for hermetically sealing the same.

The method for sterilizing bags of the present invention may be carried out manually by an operator or automatically, for example using a robotic arm for the placement of the bags in the fastening elements of the support elements.

For this, the robotic arm may perform a horizontal movement parallel to the floor in order to insert the port-plug structure of the flexible bag through the slot formed by the support elements of said flexible bags (step a) and a small vertical movement relative to the floor in order to place said bag in the fastening elements (step b) of the container of the present invention.

What is claimed is:

1. A hermetically-sealed container holding a plurality of flexible bags to be sterilized for pharmaceutical use, comprising:

an upper flat structure comprising a plurality of supports for said flexible bags, each of the supports comprising a slot and a notch;

each of the plurality of flexible bags comprising a port-plug, wherein each port-plug is inserted through the slot of one of the supports and accommodated in the notch of said one of the supports such that each flexible bag is retained within the slot and above the notch of one of the supports; and a lower receptacle containing said upper flat structure and flexible bags, wherein the lower receptacle is coupled to the upper flat structure in a detachable manner and such that the upper flat structure serves as a cap hermetically sealing said lower receptacle.

2. The hermetically-sealed container holding a plurality flexible bags to be sterilized for pharmaceutical use according to claim 1, containing from 2 to 250 flexible bags.

3. The hermetically-sealed container holding a plurality of flexible bags to be sterilized for pharmaceutical use according to claim 2, containing from 2 to 180 flexible bags.

4. The hermetically-sealed container holding a plurality of flexible bags to be sterilized for pharmaceutical use according to claim 1, wherein said container has the shape of a rectangular parallelepipedon.

5. The hermetically-sealed container holding a plurality of flexible bags to be sterilized for pharmaceutical use according to claim 1, wherein the container is made of high-density polyethylene (HDPE).

6. The hermetically-sealed container holding a plurality of flexible bags to be sterilized for pharmaceutical use according claim 1, wherein each of the supports is a bar with a T and/or L-shaped cross-section which is attached in a non-detachable manner to the upper flat structure of the container.

7. The hermetically-sealed container holding a plurality of bags to be sterilized for pharmaceutical use claim 1, wherein said notches are semi-circle-shaped notches made in said supports.

8. The hermetically-sealed container holding a plurality of flexible bags to be sterilized for pharmaceutical use according to claim 7, wherein said semi-circle has a diameter greater than the port-plug of the flexible bag, but smaller than the diameter of a flange of the port-plug of said bag.

9. A method for filling/sterilizing the hermetically-sealed container for sterilizing flexible bags according to claim 1, the method comprising:
 a) inserting the port-plug structure of a flexible bag through a slot formed by the supports of said flexible bags at an insertion region, which elements are located in the upper flat structure of said container;
 b) placing said bag in the notch which is furthest from the insertion region of said bag through the support elements;
 c) inserting new flexible bags through the support elements until all the notches of the upper flat structure of said container are full;
 d) inserting said upper flat structure into the lower receptacle of the container;
 e) sterilizing said container.

10. The method according to claim 9, wherein the new flexible bags are gradually placed in such a way that a first row of bags in the notches furthest from the insertion region of said bag through the supports is filled.

11. The method according to claim 10, wherein the first row of bags are alternately formed.

12. The method according to claim 9, wherein the sterilization in step (e) is carried out by using gamma rays or electron beam (E-beam).

13. The method according to claim 9, wherein said method is carried out manually.

14. The method according to claim 9, wherein said method is carried out automatically using a robotic arm.

15. The method according to claim 14, wherein said robotic arm makes a horizontal movement parallel to the floor in order to insert the port-plug structure of the flexible bag through the slot formed by the supports of said flexible bags (step a) and a vertical movement towards the floor in order to place said bag in the notches (step b) of said container.

* * * * *